US006540724B1

(12) United States Patent
Harris

(10) Patent No.: US 6,540,724 B1
(45) Date of Patent: Apr. 1, 2003

(54) CATHETER COVER

(76) Inventor: Kavara Harris, 4541 St. John's Ave., Dayton, OH (US) 45406

( * ) Notice: Subject to any disclaimer, the term of this patent is extended or adjusted under 35 U.S.C. 154(b) by 181 days.

(21) Appl. No.: 09/594,903

(22) Filed: Jun. 15, 2000

Related U.S. Application Data

(60) Provisional application No. 60/142,093, filed on Jul. 2, 1999.

(51) Int. Cl.⁷ .............................................. A61M 5/32
(52) U.S. Cl. ...................................... 604/174; 607/104
(58) Field of Search ................................ 604/174, 179, 604/344; 602/41; 2/102; 607/104

(56) References Cited

U.S. PATENT DOCUMENTS

| | | | |
|---|---|---|---|
| 3,714,947 A | * 2/1973 | Hardy .......................... 607/104 |
| 4,582,508 A | 4/1986 | Pavelka |
| 4,666,432 A | 5/1987 | McNeish et al. |
| 4,799,923 A | 1/1989 | Campbell |
| 4,973,314 A | 11/1990 | Garrett |
| 5,048,122 A | 9/1991 | Prieur |
| 5,140,996 A | 8/1992 | Sommers et al. |
| 5,364,367 A | * 11/1994 | Banks et al. ................. 604/174 |
| 5,403,285 A | 4/1995 | Roberts |
| 5,415,642 A | * 5/1995 | Shepherd ..................... 604/344 |
| 5,449,349 A | 9/1995 | Sallee et al. |
| D377,831 S | 2/1997 | Bierman |
| 5,605,546 A | * 2/1997 | Wolzinger et al. ........... 604/174 |
| 5,707,348 A | 1/1998 | Krogh |
| 6,032,289 A | * 3/2000 | Villapiano ..................... 2/102 |
| 6,126,639 A | * 10/2000 | Sutherland et al. .......... 604/179 |
| 6,222,090 B1 | * 4/2001 | Weston ......................... 602/41 |
| 6,258,066 B1 | * 7/2001 | Urich .......................... 604/174 |
| 6,273,873 B1 | * 8/2001 | Fleischer ..................... 604/174 |
| 6,290,676 B1 | * 9/2001 | Bierman ...................... 604/174 |

FOREIGN PATENT DOCUMENTS

DE 29718185 * 2/1998 ........... A61F/13/00

OTHER PUBLICATIONS

Print-out of Web page—http://www.baboospatch.com (19 pages).

* cited by examiner

Primary Examiner—Teresa Walberg
Assistant Examiner—L Fastovsky
(74) Attorney, Agent, or Firm—Bose McKinney & Evans LLP

(57) ABSTRACT

A self-supporting catheter cover for holding and covering the external tubes of an intravenous therapy device. The cover includes first and second panels defining a pocket in communication with an open top edge. Releasable securing means are fixed to the first and second panels proximate the top edge for frictionally engaging and retaining an external tube of the catheter such that the cover is supported by the catheter. As such the cover does not require independent securing devices for attachment to the body of the patient.

20 Claims, 6 Drawing Sheets

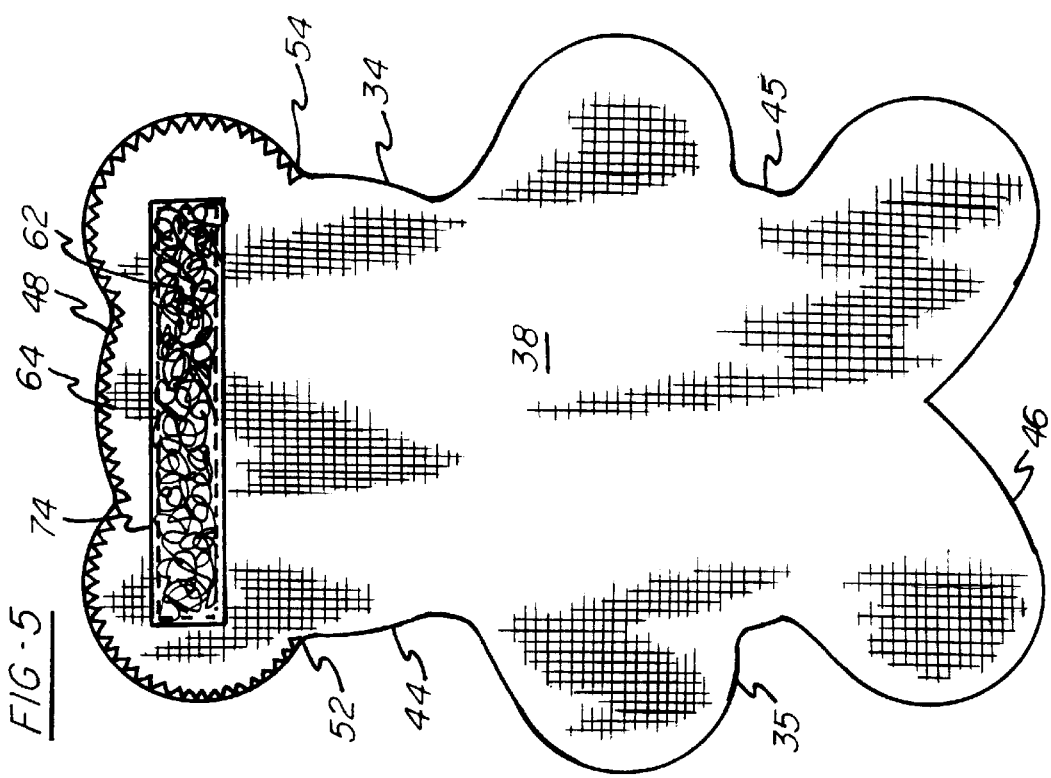
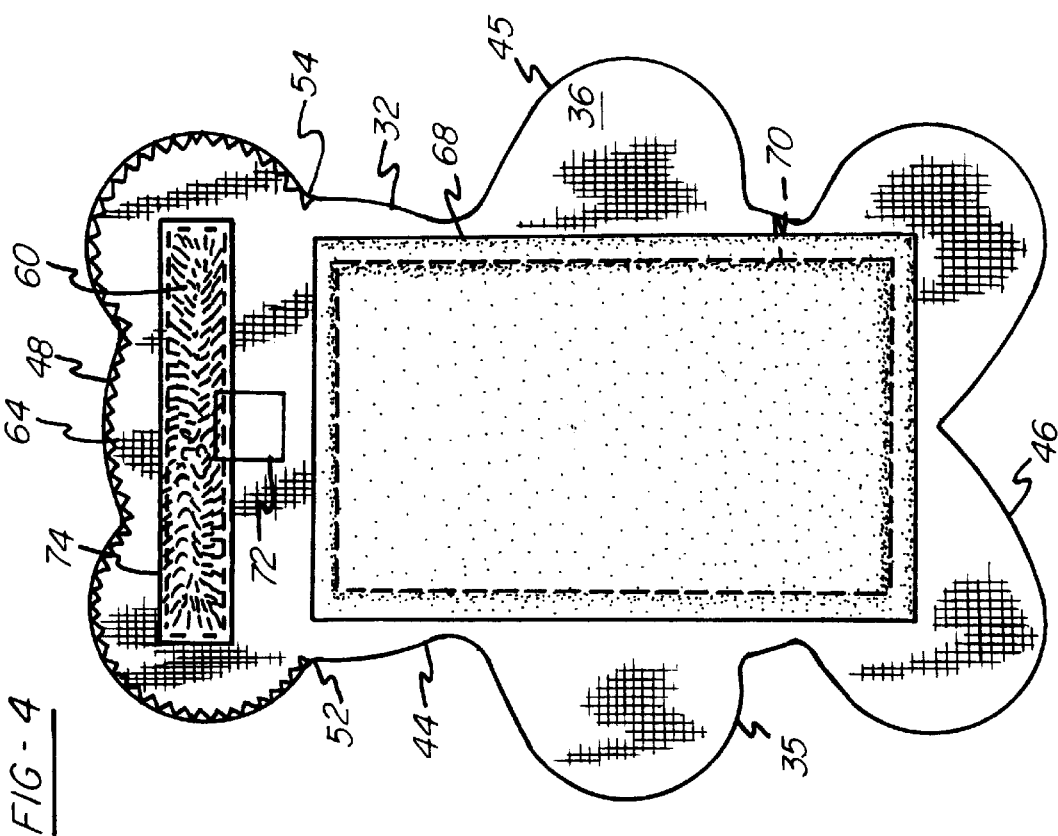

CATHETER COVER

CROSS-REFERENCE TO RELATED APPLICATION

This application claims the benefit of U.S. Provisional Patent Application Ser. No. 60/142,093, filed Jul. 2, 1999.

BACKGROUND OF THE INVENTION

1. Field of the Invention

The present invention relates generally to an apparatus for use with intravenous therapy devices and, more particularly, to an apparatus for holding and covering a catheter tube implanted within the body of an individual.

2. Description of the Prior Art

Surgically implanted intravenous therapy devices such as central venous catheters, are often used for prolonged treatment of blood disorders and cancer by providing permanent internal tubing received within the blood distribution system proximate the heart of a patient for the administering of medication and other substances as well as for periodic blood testing. As illustrated in FIG. 1, the catheter may comprise a flexible silicone tube 12 having a tip which is placed in a large vein near the heart and brought under the skin along the chest wall to leave the body at an exit site 14. The external tubing of the tube 12 may split into individual external tubes 16 and 18, often called "central lines," at a joint 20. A clamping device 22 may be provided to cooperate with the external tubes 16 and 18 to prevent the flow of fluid into or out of the tube 12. Caps 24 and 26 are provided at the free ends of the tubes 16 and 18 which allow for the insertion of liquid medications or the withdrawal of blood.

Typically, the external tubes 16 and 18 of the implanted catheter 10 are taped to the body of the patient to prevent displacement and dislodgement of the catheter 10. To use the caps 24 and 26 of the catheter 10, it is therefore necessary to remove the tape 27 securing the tubes 16 and 18 to the body. Such removal and reapplying of the tape 27 is often discomforting and irritating to the patient. Additionally, the appearance of the taped external tubes 16 and 18 on the body often presents an unsightly and mentally disturbing appearance in many patients, particularly children.

In apparent recognition of the undesirability of taping the catheter 10 to the body of the patient, attempts have been made to design catheter covers or protection devices which eliminate the necessity of taping the external tubes 16 and 18 to the body of the patient. Examples of such prior art catheter protection devices are illustrated in U.S. Pat. Nos. 4,666,432, 5,048,122 and 5,403,285. However, all of the aforementioned prior art catheter protection devices still require some means of securing the device to the body of the patient. Such means of securing the device to the body include belts wrapped around the chest of the patient and specially designed garments designed to hold the catheter tubes 16 and 18. Such devices are often irritating to the patient as providing an additional article which must be attached to the body. Additionally, such body supported devices may provide a hazard where a portion of the device may be caught on external surfaces.

Accordingly, there is a need for a catheter cover which is supported independently of the body of the patient and does not require the use of securing devices to attach the cover to the patient.

SUMMARY OF THE INVENTION

The present invention provides a catheter cover which is adapted to securely engage external tubing of an implanted catheter without requiring additional securing devices for attaching the cover to the body of the patient.

The catheter cover of the present invention includes first and second panels each having an inner surface, an outer surface and a peripheral edge, which is formed to define a profile which is of a pleasing appearance to children. The first and second panels are preferably formed from a lightweight, soft fabric which is machine washable and dryable. The inner surfaces of the first and second panels may be defined by an interface material. The first and second panels are secured together with their inner surfaces facing towards each other to define a pocket. More particularly, a connector extends along a substantial portion of the peripheral edges of the first and second panels for securing the panels in an overlapping relationship. The peripheral edge preferably comprises opposing side edges connecting a bottom edge to a top open edge, which has an arc of approximately 100°, as measured from a center point of the panels, between first and second ends of the connector.

A releasable securing device, preferably a hook and loop fastener, extends substantially along the length of the top edge for releasably securing the external tubing of the catheter while a free end of the external tubing is received within the pocket. The releasable securing device extends substantially around the outer surface of the external tubing in frictional engagement therewith, such that the cover is self-supporting on the catheter. As such, no external fastening means are needed to secure the cover to the body of the patient.

Therefore, it is an object of the invention to provide a comfortable and lightweight catheter cover which eliminates the need for external patient securing devices.

It is another object of the invention to provide a pleasant, cheerful and aesthetically pleasing catheter cover.

It is a further object of the invention to provide such a catheter cover which is inexpensive to produce and easy to maintain.

It is yet another object of the invention to provide such a catheter cover which may be worn by children with implanted catheters.

It is a further object of the invention to provide a catheter cover which may be used with a wide variety of different sizes and designs of catheters.

Other objects and advantages of the invention will be apparent from the following description, the accompanying drawings and the appended claims.

BRIEF DESCRIPTION OF THE DRAWINGS

FIG. 4 is a front elevational view of the inside surface of a first panel of the catheter cover of the present invention;

FIG. 5 is a front elevational view of the inside surface of a second panel of the catheter cover of the present invention;

DETAILED DESCRIPTION OF THE PREFERRED EMBODIMENT

Figure 8:
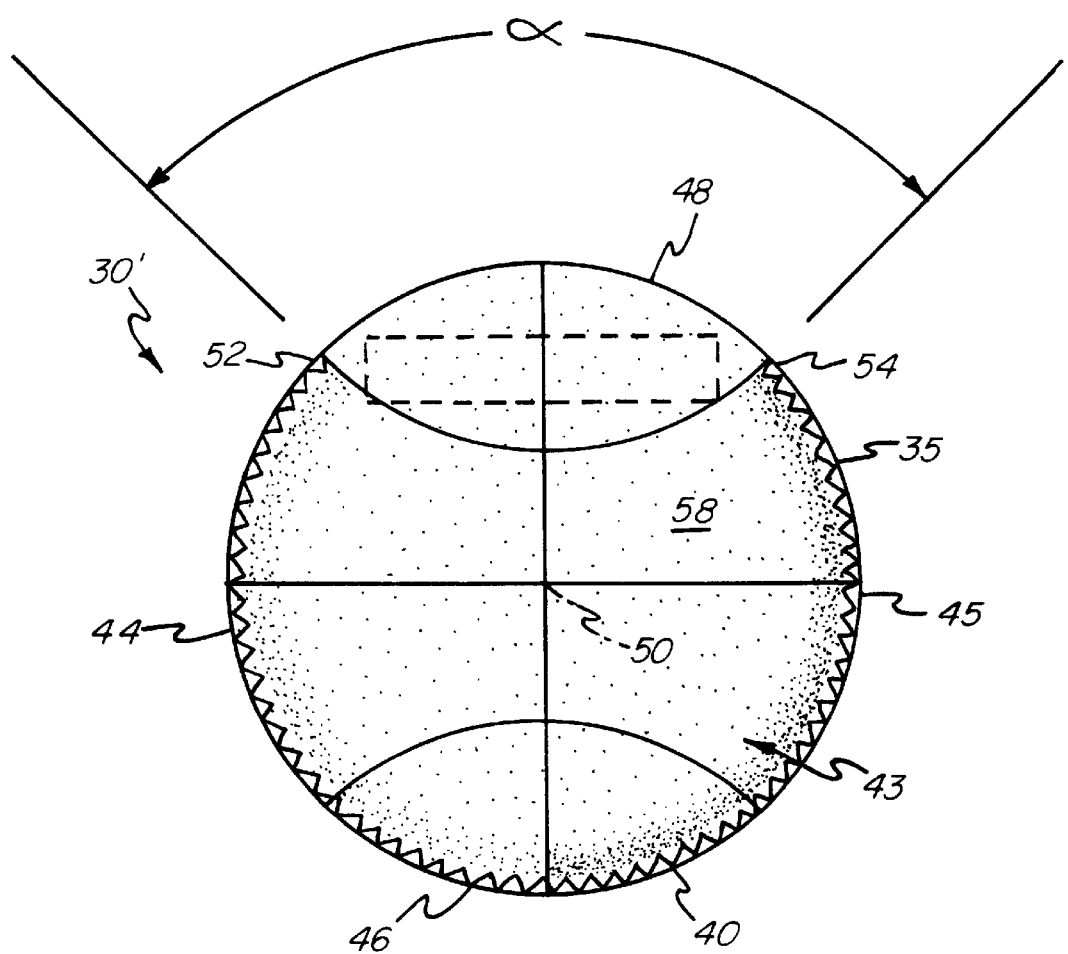
FIG. 8 is a front elevational view of an alternative embodiment of the catheter cover of the present invention.

Referring initially to FIGS. 1–5, the catheter cover 30 of the present invention includes first and second panels 32 and 34 which are formed in an identical shape. The panels 32 and 34 are preferably cut from a craft velour fabric although any comparable lightweight soft fabric which does not easily fray and which is machine washable and dryable may be readily substituted therefor. The first and second panels 32 and 34 each include a peripheral edge 35 which preferably defines a profile shape which is aesthetically pleasing to the patient, particularly children. As such, the catheter cover 30 may have the shape of a teddy bear, dinosaur or other animal. Likewise, the peripheral edge 35 of the catheter cover 30' may have the shape of a circle and, moreover, of a sports related objects, such as a basketball (FIG. 8).

Figure 7:
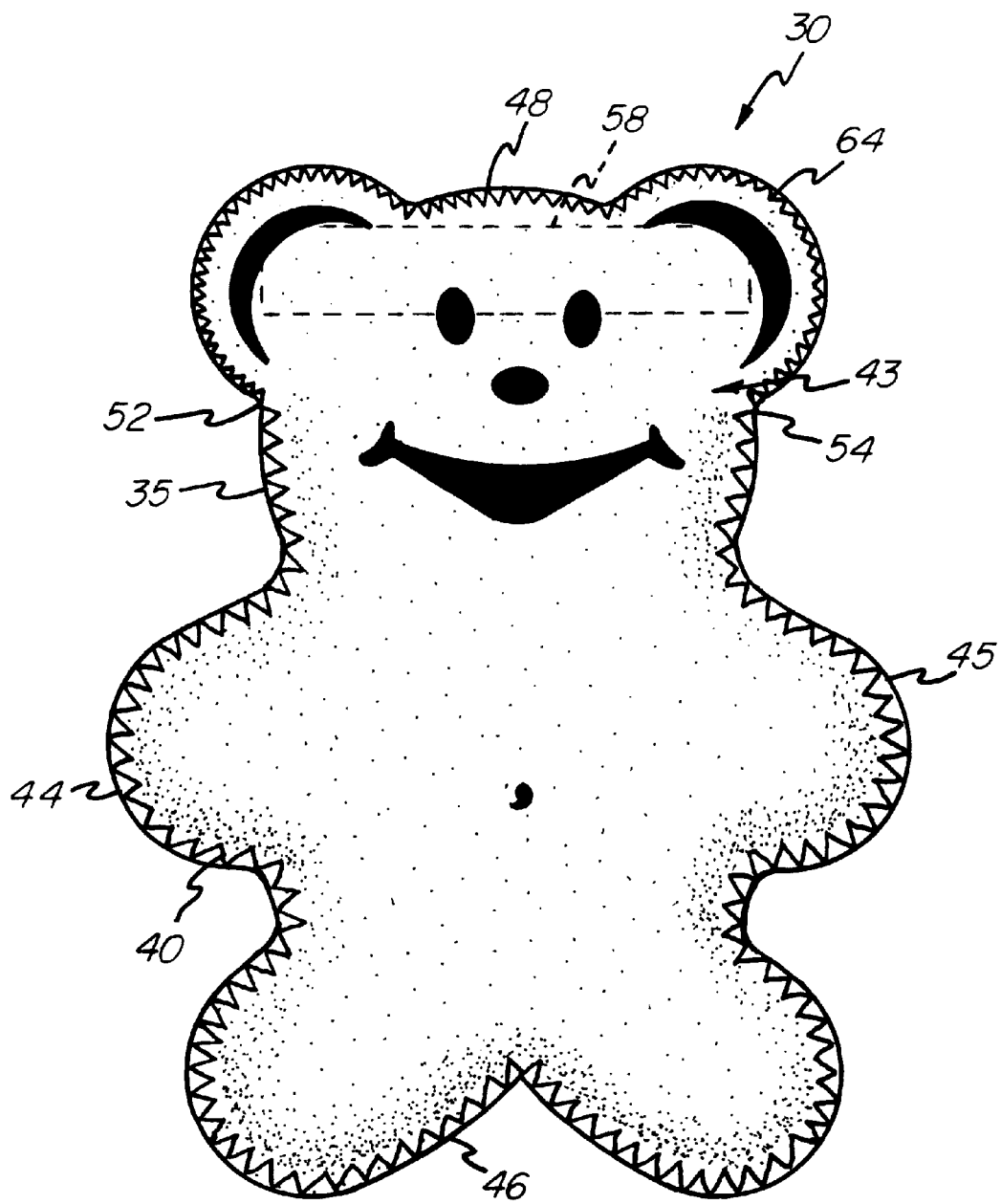
FIG. 7 is a front elevational view of a first embodiment of the catheter cover of the present invention.

Interfacing material may define the inner surfaces 36 and 38 of the first and second panels 32 and 34, respectively, when lightweight material is used for the first and second panels 32 and 34. While the interfacing preferably comprises Armo-Weft Tailoring Interfacing, similar interfacing materials may be readily substituted therefor. Typically, such interfacing material is not required when heavier material such as craft velour is utilized. The inner surfaces 36 and 38 of the first and second panels 32 and 34 are positioned in facing relation to each other and then secured by a connector 40. The outer surfaces 41 and 42 of the panels 32 and 34 may include visually appealing indicia 43 as illustrated in FIGS. 7 and 8.

Figure 2:
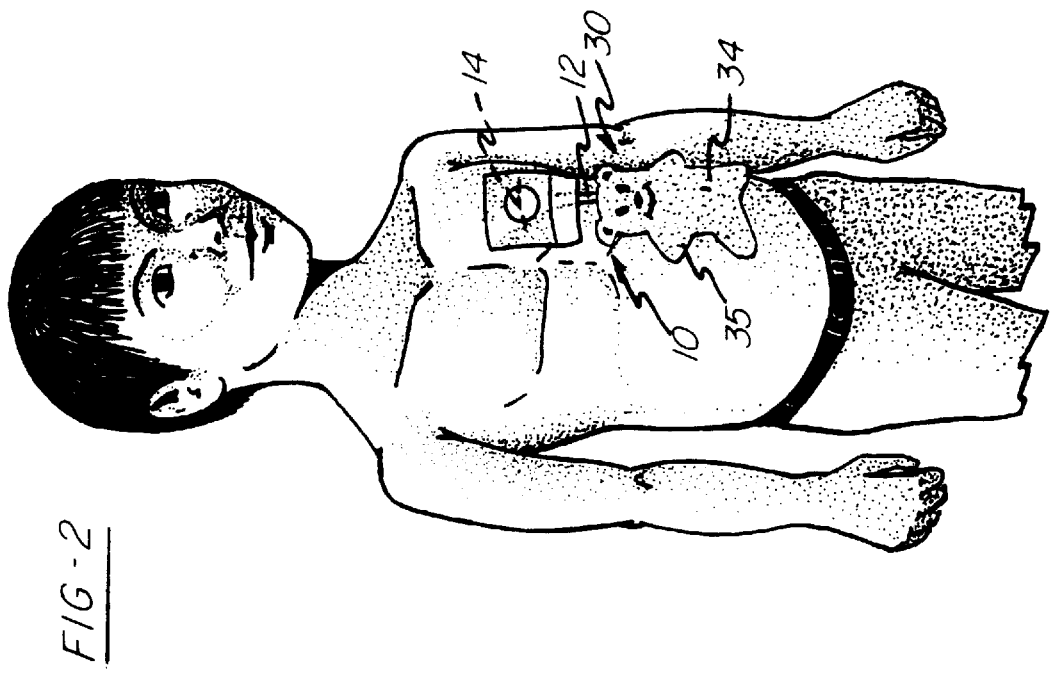
FIG. 2 is a perspective view of the catheter cover of the present invention secured to the catheter of FIG. 1.
Figure 1:
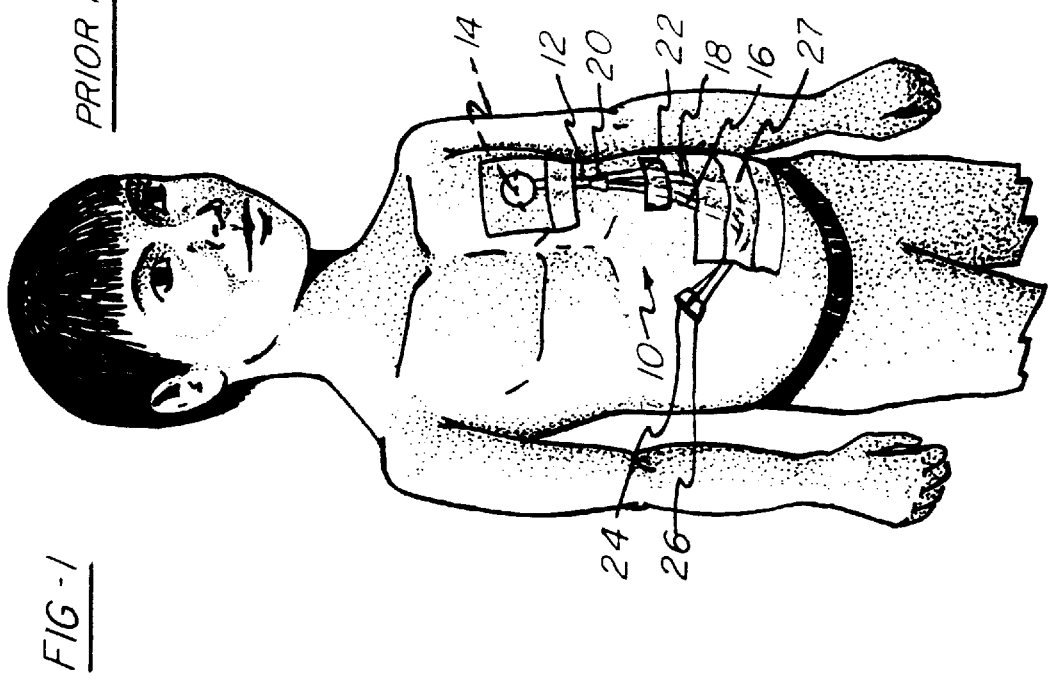
FIG. 1 is a perspective view of a conventional catheter implanted within the body of a patient.
Figure 3:
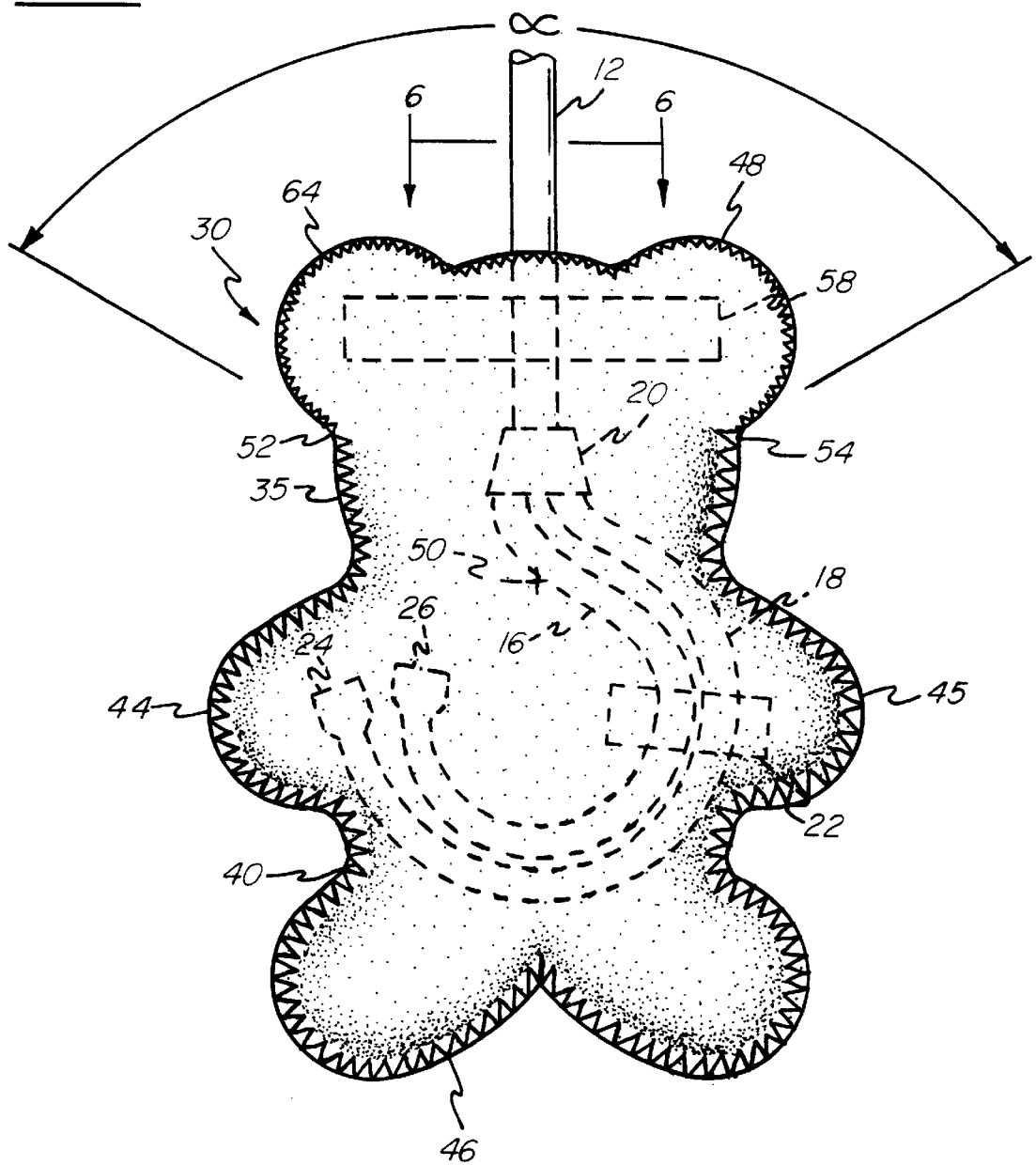
FIG. 3 is a front elevational view of the catheter cover of the present invention as applied to the catheter of FIG. 1.

The peripheral edge 35 of each of the panels 32 and 34 includes side edges 44 and 45, a bottom edge 46 and a top edge 48 wherein the side edges 44 and 45 interconnect the bottom and top edges 46 and 48. The connector 40 extends proximate the first and second side edges 44 and 45 and the bottom edge 46 wherein the top edge 48 remains open. More particularly, the connector 40 extends substantially around the peripheral edge 35 of the catheter cover 30 such that an arc, as measured from a center point 50 of the panels 32 and 34, has an angular dimension of α from a first end point 52 to a second end point 54 of the connector 40, wherein α has a value of approximately 100° (FIG. 3). The connector 40 preferably comprises a looped stitch line which extends partially over a portion of the peripheral edge 35 in a counterclockwise direction from first end point 52 to second end point 54. The looped stitch line provides a visually pleasing appearance as opposed to other available connectors 40. However, it should be appreciated that similar securing means, including adhesives and heat bonding, may be readily substituted for the stitch line.

Figure 6:
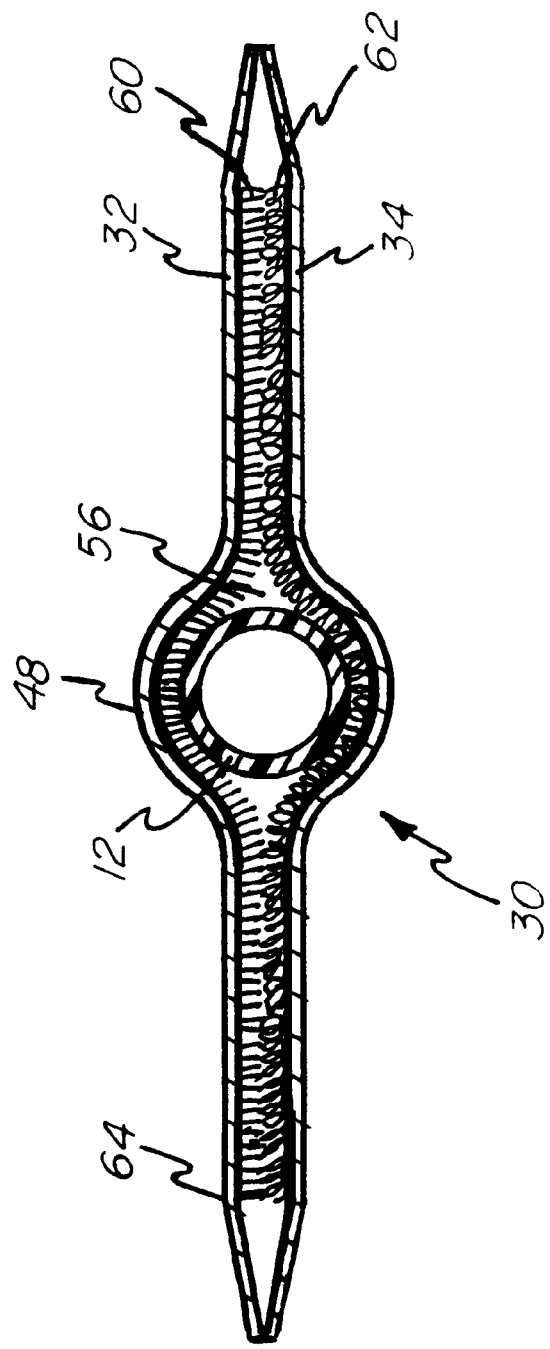
FIG. 6 is a cross-sectional view taken along line 6—6 of FIG. 3.

A pocket 56 is defined between the inside surfaces 36 and 38 of the first and second panels 32 and 34 and the connector 40 for receiving the free ends or caps 24 and 26 of the catheter 10 (FIGS. 3 and 6). A releasable securing device 58 extends substantially across the width of the top edge 48 such that the pocket 56 may be closed. More particularly, the releasable securing device 58 preferably comprises a hook and loop fastener wherein the hook portion 60 is secured to the inside surface of the first panel 32 (FIG. 4) and the loop portion 62 is attached to the inside surface of the second panel 34 (FIG. 5). A stitch line 64 preferably extends in a clockwise direction from the first end point 52 to the second end point 54 in order to prevent fraying along the top edge 48 of each respective panel 32 and 34 and to provide an aesthetically pleasing appearance.

Referring further to FIG. 4, a comfort pad 68 is preferably fixed to the inner surface 36 of the first panel 32 by a stitch line 70. The comfort pad 68 comprises a soft padding material, preferably fleece, for cushioning the catheter 10 from the body of the patient. Additionally, an identification tag 72 is preferably fixed to the inner surface 36 of the first panel 32 beneath the hook portion 60 of the releasable securing device 58.

In operation, the free ends or caps 24 and 26 of the external tubes 16 and 18 are placed within the pocket 56 of the catheter cover 30 with a portion of the tube 12 extending out through the top edge 48. As illustrated in FIG. 6, the releasable securing device 58 substantially surrounds the tube 12 in frictional engagement therewith such that the cover 30 is self-supported upon the catheter tube 12. As such, the external tubing of the catheter 12 solely supports the cover 30 wherein the cover 30 is freely suspended from the body of the patient and no external attachment means are necessary for connecting the cover 30 to the body of the patient.

The method of manufacturing the catheter cover 30 of the present invention begins by attaching interfacing to one surface of a material, preferably velour. As mentioned above, such interfacing may be eliminated if the material of the first and second panels 32 and 34 is sufficiently dense. The material is then cut to form the first and second panels 32 and 34 of desired shape through either tracing a pattern or die cutting.

The hook portion 60 of the hook and loop fastener 58 is fixed to the inside surface 36 of the first panel 32 while the loop portion 62 is fixed to the inside surface 38 of the second panel 34 proximate the respective top edges 48. Stitching 74 may be utilized to fix the hook and loop fastener 58 to the panels 32 and 34. The comfort pad 68 is then placed in contact with the inside surface 36 of the first panel 32 and secured in place with a stitch line 70.

Next, anti-fraying material, preferably stitch lines 64 and 66 are applied to the top edge 48 of the first and second panels 32 and 34 from end point 52 to end point 54 in a clockwise direction as viewed in FIGS. 4 and 5. The inside surfaces 36 and 38 of the first and second panels 32 and 34 are then positioned so they are facing each other and connecting line 40 is formed, preferably by stitching from first end point 52 to second end point 54 in a counterclockwise direction as viewed in FIG. 3.

While the form of apparatus herein described constitutes a preferred embodiment of this invention, it is to be understood that the invention is not limited to this precise form of apparatus, and that changes may be made therein without departing from the scope of the invention which is defined in the appended claims.

What is claimed is:

1. A self-supporting catheter cover for a surgically implanted catheter including internal tubing received within the body of an individual and external tubing having a free end extending from the body, said catheter cover comprising:

a first panel including an inner surface, an outer surface and a peripheral edge;

a second panel including an inner surface, an outer surface and a peripheral edge, said inner surface of said second panel facing said inner surface of said first panel, and said peripheral edges of said first and second panels substantially aligned;

a connector extending along a substantial portion of said peripheral edges of said first and second panels for securing said first and second panels in an overlapping relationship;

a pocket defined intermediate said inner surfaces of said first and second panels for receiving the free end of the external tubing of the catheter;

a releasable securing device positioned proximate a portion of said peripheral edges of said first and second panels; and wherein the external tubing of the catheter is configured to pass through said securing device, and said securing device is configured to engage the external tubing such that said catheter cover is supported by the external tubing.

2. The catheter cover of claim 1 wherein:

said peripheral edge of each of said first and second panels includes a top edge, a bottom edge and opposing side edges interconnecting said top edge and said bottom edge;

said connector extends proximate said opposing side edges and said bottom edge; and said releasable securing device is positioned proximate said top edge.

3. The catheter cover of claim 2 wherein:

each of said first and second panels include a center point; and said connector extends between first and second points, said first and second points defining an arc proximate said top edge, said arc having an angle of approximately 100 degrees as measured from said center point of said first and second panels.

4. The catheter cover of claim 1 further comprising a comfort pad fixed to said first panel.

5. The catheter cover of claim 1 further comprising indicia formed on said outer surface of said second panel.

6. The catheter cover of claim 1 further comprising interface material defining said inner surfaces of said first and second panels.

7. The catheter cover of claim 1 wherein said releasable securing device comprises a hook and loop fastener, said hook and loop fastener including a hook portion fixed to said inner surface of one of said first and second panels and a loop portion fixed to said inner surface of the other of said first and second panels.

8. The catheter cover of claim 1 wherein said connector comprises a looped stitch line extending partially over said portion of said peripheral edge.

9. The catheter cover of claim 1 wherein said peripheral edge of each of said first and second panels is formed in the shape of an animal profile.

10. The catheter cover of claim 1 wherein said peripheral edge of each of said first and second panels is formed in the shape of a circle.

11. The catheter cover of claim 1 further comprising an antifray stitch formed along said top edge.

12. The catheter cover of claim 1 wherein said releasable securing device frictionally engages the external tubing of the catheter whereby said catheter cover is solely supported by the catheter and freely suspended from the body of the individual.

13. A catheter cover in combination with a surgically implanted catheter including internal tubing received within the body of an individual and external tubing having a free end extending from the body, said catheter cover comprising:

a first panel including an inner surface, an outer surface and a peripheral edge;

a second panel including an inner surface, an outer surface and a peripheral edge, said inner surface of said second panel facing said inner surface of said first panel;

a connector for securing said first and second panels in an overlapping relationship;

a pocket defined intermediate said inner surfaces of said first and second panels for receiving said free end of said external tubing of said catheter; and a releasable securing device positioned proximate a portion of said peripheral edges of said first and second panels for releasably securing to said external tubing of said catheter wherein said catheter cover is solely supported and freely suspended relative to the body of the individual by said external tubing.

14. The catheter cover of claim 13 wherein:

said peripheral edge of each of said first and second panels includes a top edge, a bottom edge and opposing side edges interconnecting said top edge and said bottom edge;

said connector extends proximate said opposing side edges and said bottom edge; and said releasable securing device is positioned proximate said top edge.

15. The catheter cover of claim 14 wherein:

each of said first and second panels include a center point; and said connector extends between first and second points, said first and second points defining an arc proximate said top edge, said arc having an angle of approximately 100 degrees as measured from said center point of said first and second panels.

16. The catheter cover of claim 13 further comprising a comfort pad fixed to said first panel.

17. The catheter cover of claim 13 further comprising indicia formed on said outer surface of said second panel.

18. The catheter cover of claim 13 wherein said releasable securing device comprises a hook and loop fastener, said hook and loop fastener including a hook portion fixed to said inner surface of one of said first and second panels and a loop portion fixed to said inner surface of the other of said first and second panels.

19. The catheter cover of claim 1 wherein said connector comprises a looped stitch line extending partially over a portion of said peripheral edge.

20. A catheter cover in combination with a surgically implanted catheter including internal tubing received within the body of an individual and external tubing having a free end extending from the body, said catheter cover comprising:

a first panel including an inner surface, an outer surface, and a peripheral edge;

a second panel including an inner surface, and an outer surface;

a connector for securing said first panel to said second panel;

a releasable securing device coupled to said first panel; and wherein the external tubing of the catheter is configured to pass through said securing device, and said securing device frictionally engages the external tubing such that the first panel is free to move relative to the body of the individual.

* * * * *